United States Patent [19]

Hewett et al.

[11] Patent Number: 4,940,484

[45] Date of Patent: Jul. 10, 1990

[54] HERBICIDAL METHOD COMPRISING THE USE OF DIFLUFENICAN

[75] Inventors: Richard H. Hewett, Thaxted; Brian M. Luscombe, Chelmsford, England

[73] Assignee: May and Baker Limited, Dagenham, United Kingdom

[21] Appl. No.: 74,872

[22] Filed: Jul. 17, 1987

[30] Foreign Application Priority Data

Jul. 21, 1986 [GB] United Kingdom ............... 8617741

[51] Int. Cl.⁵ ...................... A01N 43/40; A01N 37/38
[52] U.S. Cl. ......................................... 71/94; 71/108; 71/116
[58] Field of Search ..................................... 71/94, 108

[56] References Cited

U.S. PATENT DOCUMENTS

| | | | |
|---|---|---|---|
| 3,954,442 | 5/1976 | Becker et al. | 71/108 |
| 4,589,908 | 5/1986 | Schumacher et al. | 71/108 |
| 4,618,366 | 10/1986 | Cramp et al. | 71/94 |

*Primary Examiner*—Glennon H. Hollrah
*Assistant Examiner*—Amelia A. Owens
*Attorney, Agent, or Firm*—Burns, Doane, Swecker & Mathis

[57] ABSTRACT

The present invention relates to a method of controlling the growth of weeds at a cereal crop locus which comprises applying to the locus (a) diclofop, which is (R,S)-2-[4-(2,4-dichlorophenoxy)phenoxy]-propionic acid or an agriculturally acceptable salt or ester thereof and (b) diflufenican which is N-(2,4-difluorophenyl)-2-(3-trifluoromethylphenoxy)-nicotinamide.

7 Claims, 2 Drawing Sheets

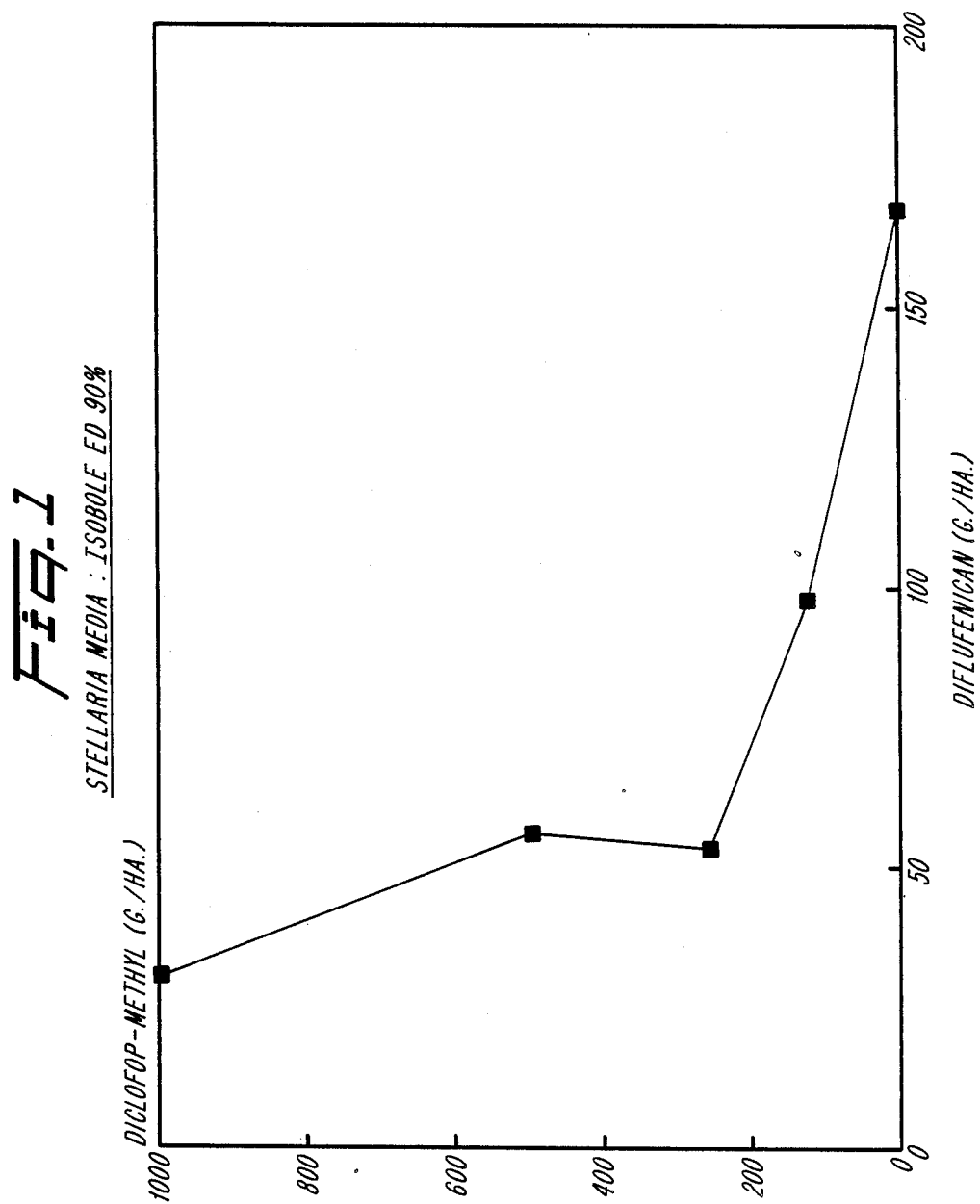

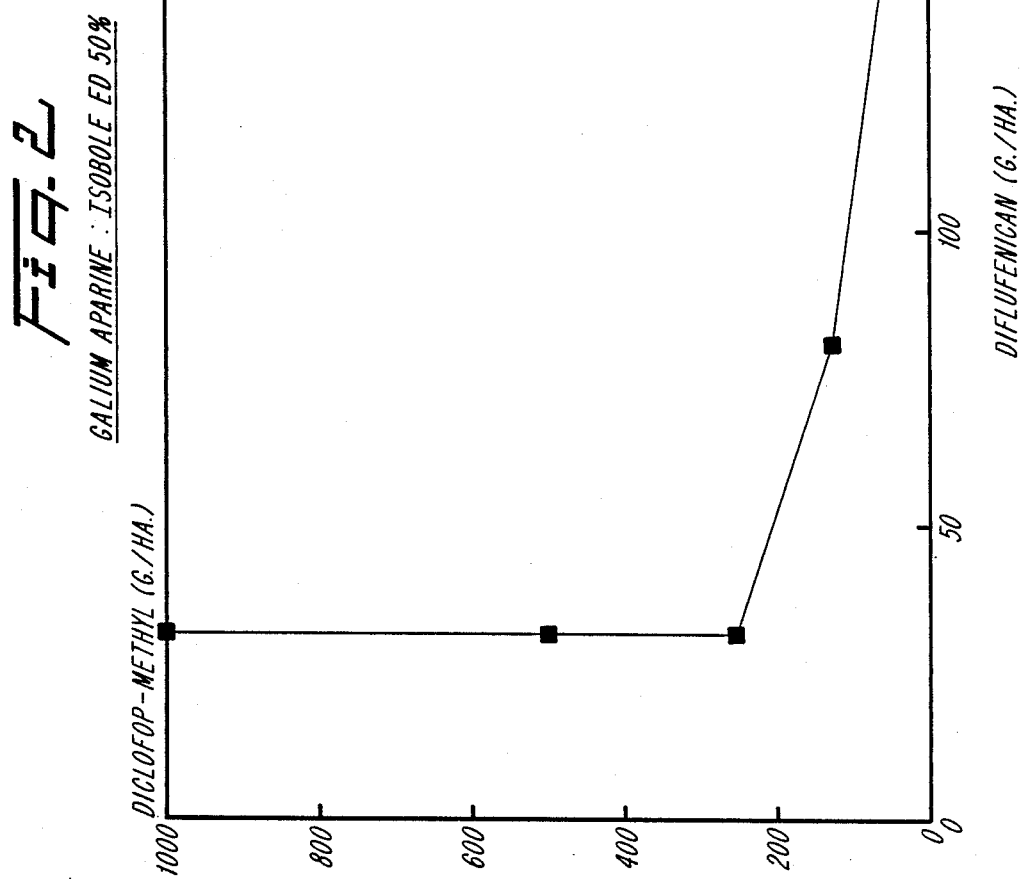

HERBICIDAL METHOD COMPRISING THE USE OF DIFLUFENICAN

The present invention relates to new herbicidal compositions comprising N-(2,4-difluorophenyl)-2-(3-trifluoromethylphenoxy) nicotinamide of the formula I depicted hereinafter, which is disclosed in the specification of British Pat. No. 2087887B as a pre- and/or post-emergence herbicide, and to their use in agriculture.

Diclofop - i.e. (R,S)-2-[4-(2,4-dichlorophenoxy)-phenoxy]propionic acid and its agriculturally acceptable salts and esters, especially diclofop-methyl, are used on a large scale for post-emergence grass weed control in cereal crops.

In this specification the term "diclofop" is meant to embrace the parent acid (acid equivalent) or an agriculturally acceptable salt or ester thereof, preferably a metal or amine salt or an alkyl ester thereof containing from 1 to 10 carbon atoms in the alkyl moiety more especially the methyl ester, diclofop-methyl, where the context so permits.

Owing to lack of residual activity in the soil diclofop does not control the weeds which emerge after application.

Diclofop has no useful activity against broad-leaf weeds, and attempts to broaden its spectrum by mixing with broad-leaf weed control materials e.g. phenoxyherbicides, have failed hitherto to yield satisfactory results.

As a result of research and experimentation it has now been discovered that the use of the compound N-(2,4-difluorophenyl)-2-(3-trifluoromethylphenoxy)-nicotinamide (hereinafter referred to for convenience as diflufenican) in combination with diclofop adds to the capabilities of the diclofop:

(a) control of a wide spectrum of broad-leaf weeds by both foliar activity and residual soil activity, and (b) residual control of annual grass weeds such as *Alopecurus myosuroides, Apera spica-venti, Digitaria sanguinalis, Echinochloa crus-galli, Poa annua* and *Poa trivialis.*

In addition to this it has been found that the combined herbicidal activity of combinations of diflufenican with diclofop against certain broad-leaf weed species is greater than expected when applied post-emergence (e.g. as a post-emergence spray), i.e. the herbicidal activity of combinations of diflufenican with diclofop showed an unexpected degree of synergism [as defined by P.M.L. Tammes, Netherlands Journal of Plant Pathology, 70 (1964), pp 73–80 in a paper entitled "Isoboles, a graphic representation of synergism in pesticides"].

The remarkable synergistic effect of the mixture applied post-emergence gives improved reliability of control of weed species occurring in cereal cultures and allows for a reduction in the amount of active ingredient employed.

Accordingly the present invention provides a method for the control of the growth of weeds at a cereal crop locus which comprises applying to the locus (a) diclofop, which is (R,S)-2-[4-(2,4-dichlorophenoxy)-phenoxy]propionic acid, or an agriculturally acceptable salt or ester thereof, preferably a metal or amine salt or an alkyl ester thereof containing from 1 to 10 carbon atoms in the alkyl moiety (preferably methyl), and (b) diflufenican, which is N-(2,4-difluorophenyl)-2-(3-trifluoromethylphenoxy) nicotinamide. Preferably the application rates of (a) and (b) are from 500 to 1500 (preferably from 550 to 1100) g acid equivalent (a.e.)/ha and from 25 to 250 g/ha respectively in proportions of 60:1 to 2:1 and preferably 44:1 to 2.2:1 of (a) to (b). The method of the invention may be used to control a broad spectrum of weed species in cereal crops, e.g. wheat or barley, by pre- or post-emergence application, more especially early post-weed emergence post-crop emergence without significant permanent damage to the crop. The combined use described above provides both foliar and residual activity.

The present invention further provides a method for the control of the growth of weeds at a cereal crop locus by pre- or post-emergence application which comprises applying to the locus (a) diclofop-methyl and (b) diflufenican, at application rates of from 570 to 1140 g/ha of (a) and from 25 to 250 g/ha of (b), in proportions of 46:1 to 2.3:1 w/w of (a) to (b), to control a broad spectrum of weed species in cereal crops, e.g. wheat or barley without significant permanent damage to the crop. The combined use described above provides both foliar and residual activity.

According to a further feature of the present invention there is provided a method according to the present invention as hereinbefore described in which in addition 4-chloro-2-methylphenoxyacetic acid (MCPA) or an agriculturally acceptable salt or ester thereof is applied preferably at an application rate of from 50 to 200 g a.e./ha.

By the term 'pre-emergence application' is meant application to the soil in which the weed seeds or seedlings are present before emergence of the weeds above the surface of the soil. By the term 'post-emergence application' is meant application to the aerial or exposed portions of the weeds which have emerged above the surface of the soil. It will be appreciated that application according to the method may be from pre- to post-weed emergence pre-crop emergence to post-weed post-crop emergence. By the term 'foliar activity' is meant herbicidal activity produced by application to the aerial or exposed portions of the weeds which have emerged above the surface of the soil. By the term 'residual activity' is meant herbicidal activity produced by application to the soil in which weed seeds or seedlings are present before emergence of the weeds above the surface of the soil, whereby seedlings present at the time of application or which germinate subsequent to application from seeds present in the soil, are controlled.

Weeds that may be controlled by the method include:- from broad-leaf weeds, *Aethusa cynapium, Abutilon theophrasti, Amaranthus retroflexus, Amsinckia intermedia, Anagallis arvensis, Anthemis arvensis, Anthemis cotula, Atriplex patula, Brassica nigra, Capsella bursa-pastoris, Chenopodium album, Cirsium arvense, Datura stramonium, Euphorbia helioscopia, Galeopsis tetrahit, Galium aparine, Lamium amplexicaule, Lamium purpureum, Matricaria inodora, Myosotis arvensis, Papaver rhoeas, Plantago lanceolata, Polygonum* spp. (e.g. *Polygonum aviculare, Polygonum convolvulus* and *Polygonum persicaria*), *Portulaca oleracea, Raphanus raphanistrum, Senecio vulgaris, Sesbania florida, Sida spinosa, Silene alba, Sinapis arvensis, Solanum nigrum, Stellaria media, Thlaspi arvense, Urtica urens, Veronica hederifolia, Veronica persica* and *Viola arvensis,* and from grass weeds, *Alopecurus myosuroides, Apera spica-venti, Agrostis stolonifera, Avena* spp. (e.g. *Avena fatua, Avena ludoviciana*), *Lolium multiflorum, Poa annua, Poa trivialis, Digitaria sanguinalis, Echinochloa crus-galli, Eleusine indica,* Seta-

*ria faberii* and *Setaria viridis* and, from sedges, *Cyperus iria* and *Eleocharis acicularis.*

In accordance with usual practice, a tank mix may be prepared prior to use by combining separate formulations of the individual herbicidal components, or separate formulations may be applied in a time-separated manner.

The following greenhouse experiment illustrates the present invention by demonstrating the synergistic activity of diclofop-methyl and diflufenican in controlling the growth of *Stellaria media* and *Galium aparine.*

EXPERIMENT 1

Greenhouse experiment showing the nature of biological synergism between diclofop-methyl and diflufenican A wide range of doses of diclofop-methyl, i.e. 125, 250, 500 and 1000 g/ha (in a composition according to Example 2 as described hereinafter), and of diflufenican, i.e. 32, 63, 125, 250 and 500 g/ha (in a composition according to Example 1 as described hereinafter), were applied at a spray volume of 290 1/ha to sets of four replicate 7.5 cm square pots of loam soil each planted with 4 *Stellaria media* seedlings at the 6 leaf stage or 4 *Galium aparine* seedlings at the 2 whorl stage. After spraying, the pots were arranged in randomised blocks in a greenhouse, watered as necessary, and assessed after 18 days for percentage phytotoxicity (reduction in green area compared with unsprayed plants)(0=no effect, 100=complete destruction).

From these results the $ED_{90}$ values (effective dose giving 90% phytotoxicity) or $ED_{50}$ values (effective dose giving 50% phytotoxicity) in grams of diflufenican per hectare, for *Stellaria media* and *Galium aparine* respectively, were calculated for diflufenican alone and for diflufenican with increasing rates of diclofop-methyl.

Diclofop-methyl applied alone was found to have no activity on *Stellaria media* and *Galium aparine.*

The $ED_{90}$ values for *Stellaria media* were as follows:

|  | $ED_{90}$ |
| --- | --- |
| Diflufenican alone | 168 |
| Diflufenican with 125 g diclofop-methyl/ha | 98 |
| Diflufenican with 250 g diclofop-methyl/ha | 53 |
| Diflufenican with 500 g diclofop-methyl/ha | 56 |
| Diflufenican with 1000 g diclofop-methyl/ha | 30 | and the $ED_{50}$ values for *Galium aparine* were:

|  | $ED_{50}$ |
| --- | --- |
| Diflufenican alone | 199 |
| Diflufenican with 125 g diclofop-methyl/ha | 81 |
| Diflufenican with 250 g diclofop-methyl/ha | <32 |
| Diflufenican with 500 g diclofop-methyl/ha | <32 |
| Diflufenican with 1000 g diclofop-methyl/ha | <32 |

The symbol "<" means "less than".

The results were then used to plot isoboles with a "one-sided effect" according to the methods of P.M.L. Tammes, op. cit. The isoboles produced, shown hereinafter in FIGS. I and II, were clearly type II curves (Tammes, op. cit., page 74), characteristic of synergism.

According to a further feature of the present invention, there is provided a product comprising (a) diclofop or an agriculturally acceptable salt or ester thereof, preferably a metal or amine salt or an alkyl ester thereof containing from 1 to 10 carbon atoms in the alkyl moiety and (b) diflufenican as a combined preparation for simultaneous, separate or sequential use in controlling the growth of weeds at a cereal crop locus.

According to a further feature of the present invention, there are provided compositions suitable for herbicidal use comprising (a) diclofop or an agriculturally acceptable salt or ester thereof, preferably a metal or amine salt or an alkyl ester thereof containing from 1 to 10 carbon atoms in the alkyl moiety and (b) diflufenican for example in proportions of 60:1 to 2:1 preferably 44:1 to 2.2:1, wt/wt of acid equivalent (a) to (b) in association with, and preferably homogeneously dispersed in, one or more compatible herbicidally-acceptable diluents or carriers and/or surface-active agents (i.e. diluents or carriers or surface-active agents of the type generally accepted in the art as being suitable for use in herbicidal compositions and which are compatible with diclofop and diflufenican). The term "homogeneously dispersed" is used to include compositions in which diclofop and diflufenican are dissolved in the other components. The term "herbicidal compositions" is used in a broad sense to include not only compositions which are ready for use as herbicides but also concentrates which must be diluted before use. Preferably, the compositions contain from 0.05 to 90% by weight of diclofop and diflufenican.

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, products based on condensates of ethylene oxide with nonyl- or octylphenols, or carboxylic acid esters of anhydrosorbitols which have been rendered soluble by etherification of the free hydroxy groups by condensation with ethylene oxide, alkali and alkaline earth metal salts or sulphuric acid esters and sulphonic acids such as dinonyl- and dioctyl-sodium sulphono-succinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding diclofop and diflufenican with solid diluents or by impregnating the solid diluents or carriers with solutions of diclofop and diflufenican in volatile solvents, evaporating the solvents and, if necessary, grinding the products so as to obtain powders. Granular formulations may be prepared by absorbing diclofop and diflufenican (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of diclofop and diflufenican may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% w/v of diclofop and diflufenican, from 2 to 10% w/v of surface-active agent, from 0.1 to 5% w/v of thickener and from 15 to 87.9% by volume of water; wettable powders which comprise from 10 to 90% w/w of diclofop and diflufenican, from 2 to 10% w/w of surface-active agent and from 8 to 88% w/w of solid diluent or carrier; liquid water soluble concentrates which comprise from 10 to 30% w/v of diclofop and diflufenican, from 5 to 25% w/v of surface-active agent and from 45 to 85% by volume of water-miscible solvent, e.g. dimethylformamide; liquid emulsifiable suspension concentrates which comprise 10 to 70% w/v of diclofop and diflufenican, from 5 to 15% w/v of surface-active agent, from 0.1 to 5% w/v of thickener and from 10 to 84.9% by volume of organic solvent; granules which comprise from 2 to 10% w/w of diclofop and diflufenican, from 0.5 to 2% w/w of surface-active agent and from 88 to 97.5% w/w of granular carrier and emulsifiable concentrates which comprise from 0.05 to 90% w/v, and preferably from 1 to 60% w/v, of diclofop and diflufenican, from 0.01 to 10% w/v, and preferably from 1 to 10% w/v, of surface-active agent and from 9.99 to 99.94%, and preferably from 39 to 98.99%, by volume of organic solvent.

Herbicidal compositions according to the present invention may also comprise diclofop and diflufenican in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, for example benzoylprop-ethyl [ethyl N-benzoyl-N-(3,4-dichlorophenyl-2-aminopropionate], chlorfenpropmethyl [methyl 2-chloro-2-(4-chlorophenyl)propionate], chlortoluron [N'-(3-chloro-4-methylphenyl)-N,N-dimethylurea]-cyanazine [2-chloro-4-(1-cyano-1-methylethyl-amino)-6-ethylamino-1,3,5-triazine], difenzoquat [1,2-dimethyl-3,5-diphenylpyrazolium salts], diuron [N'-(3,4-dichlorophenyl)-N,N-dimethylurea], flamprop-isopropyl [isopropyl (±)-2-(N-benzoyl-3-chloro-4-fluoroanilino) propionate], flamprop-methyl [methyl (±)-2-(N-benzoyl-3-chloro-4-fluoroanilino)propionate]isoproturon [N'-(4-isopropylphenyl)-N,N-dimethylurea]linuron [N'-(3,4-dichlorophenyl)-N-methoxy-N-methylurea], methabenzthiazuron [N-(benzothiazol-2-yl)-N,N'-dimethylurea], tri-allate [S-2,3,3-trichloroallyl N,N-di-isopropylthiocarbamate]and trifluralin [2,6-dinitro-N,N-dipropyl-4-trifluoromethylaniline]; insecticides, e.g. carbaryl [naphth-1-yl N-methylcarbamate]and synthetic pyrethroids, e.g. permethrin and cypermethrin; and fungicides, e.g. 2,6-dimethyl-4-tridecyl-morpholine, methyl N-(1-butylcarbamoylbenzimidazol-2-yl)carbamate, 1,2-bis-(3-methoxycarbonyl-2-thioureido)benzene, isopropyl 1-carbamoyl-3-(3,5-dichlorophenyl)-hydantoin and 1-(4-chlorophenoxy)-3,3'-dimethyl-1-(1,2,4-triazol-1-yl) butan-2-one. Other biologically active materials which may be included in, or used in conjunction with, the herbicidal compositions of the present invention are plant growth regulators, e.g. succinamic acid, (2-chloroethyl)trimethylammonium chloride and 2-chloroethanephosphonic acid; and fertilizers containing, for example, nitrogen, potassium and phosphorus and trace elements known to be essential to successful plant life, e.g. iron, magnesium, zinc, manganese, cobalt and copper.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

Preferred herbicidal compositions according to the present invention which comprise diclofop and diflufenican in association with another herbicide are those wherein the other herbicide is MCPA or an agriculturally acceptable salt or ester thereof.

The compositions of the invention may be made up as an article of manufacture comprising diclofop and diflufenican and optionally other biologically active compounds as hereinbefore described or, as is preferred, a herbicidal composition as hereinbefore described, and preferably a herbicidal concentrate which must be diluted before use, comprising diclofop and diflufenican within a container for the aforesaid diclofop and diflufenican or a said herbicidal composition, and instructions physically associated with the aforesaid container setting out the manner in which the aforesaid diclofop and diflufenican or herbicidal composition contained therein is to be used to control the growth of weeds. The containers will normally be of the types conventionally used for the storage of chemical substances which are solids at normal ambient temperatures and herbicidal compositions, particularly in the form of concentrates, for example cans and drums of metal, which may be internally-lacquered, and plastics materials, bottles of glass and plastics materials and, when the contents of the container is a solid, for example granular herbicidal compositions, boxes, for example of cardboard, plastics materials and metal, or sacks. The containers will normally be of sufficient capacity to contain amounts of the active ingredients or herbicidal compositions sufficient to treat at least 0.5 hectares of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 500 g and 1500 g a.e. of diclofop and between 25 g and 250 g of diflufenican per hectare in the manner and for the purposes hereinbefore described.

The following Examples illustrate herbicidal compositions according to the present invention.

EXAMPLE 1

An aqueous suspension concentrate was made from:

| | |
|---|---|
| diflufenican | 50% w/v |
| ethylene glycol | 5% w/v |
| Ethylan BCP (nonylphenol ethylene oxide condensate containing 9 moles ethylene oxide) | 0.5% w/v |
| Soprophor FL (triethanolamine salt of oxyethylated polyarylphenolphosphate) | 1.0% w/v |
| Sopropon T36 (sodium polycarboxylate) | 0.5% w/v |
| Antifoam FD (silicone antifoam) | 0.1% w/v |
| Rhodigel 23 (xanthan gum) | 0.2% w/v |
| dichlorophen sodium solution, 40% w/w | 0.25% w/v |
| water | to 100% by volume | by blending the diflufenican with an aqueous solution of the Soprophor FL, Sopropon T36, Antifoam FD and Ethylan BCP and milling through a bead-mill. An aqueous solution of the Rhodigel 23, dichlorophen sodium solution and ethylene glycol is then blended with the milled slurry and made up to volume with water.

EXAMPLE 2

An emulsifiable concentrate was formed from:

| | |
|---|---|
| diclofop-methyl | 30% w/v |
| Soprophor BSU (tristyryl phenol ethylene oxide condensate containing 15 moles ethylene oxide) | 3% w/v |
| Arylan CA (calcium dodecylbenzene sulphonate) | 5% w/v |
| Solvesso 150 (light aromatic C10 hydrocarbon) | to 100% by volume | by adding with stirring the diclofop-methyl to a solution of the soprophor BSU and Arylan CA in some of the Solvesso 150. When fully dissolved, further Solvesso 150 is added to volume.

EXAMPLE 3

An emulsifiable concentrate was formed from:

| | |
|---|---|
| diflufenican | 2% w/v |
| diclofop-methyl | 16% w/v |
| Soprophor BSU | 3% w/v |
| Arylan CA | 5% w/v |
| cyclohexanone | 25% w/v |
| Solvesso 150 | to 100% by volume | by adding with stirring the diflufenican and diclofop-methyl to a solution of the Soprophor BSU and Arylan CA in the cyclohexanone. When fully dissolved, Solvesso 150 is added to volume.

Five liters of the resulting formulation were diluted in 200 litres of water and applied post-emergence to 1 hectare of winter wheat to control *Stellaria media, Veronica persica, Viola arvensis* and *Avena fatua*.

EXAMPLE 4

A 60:1 mixture was formed by tank mixing 5 l of the composition of Example 2 with 50 ml of the composition of Example 1 in a volume of 200 l of water. The resulting spray fluid was applied to one hectare of winter wheat to control *Avena fatua* and *Viola arvensis*.

EXAMPLE 5

A 2:1 mixture was formed by tank mixing 1667 ml of the composition of Example 2 with 500 ml of the composition of Example 1 in a volume of 200 l of water. The resulting spray fluid was applied to one hectare of winter wheat to control *Avena fatua, Poa annua, Viola arvensis, Veronica hederifolia* and *Galium aparine*.

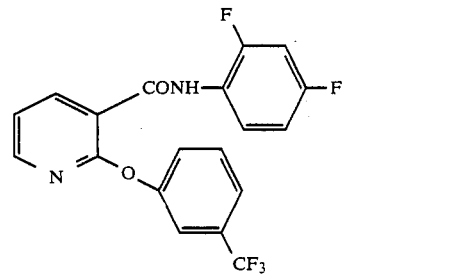

We claim:
1. A method of controlling the growth of the weeds *Stellaria media* and *Galium aparine* at a cereal crop locus which comprises applying to the locus an effective amount of the combination of (a) diclofop-methyl, which is the methyl ester of (R,S)-2-[4-1(2,4-dichlorophenoxy)phenoxy]propionic acid, and (b) diflufenican which is N-(2,4-difluorophenyl)-2(3-trifluoromethylphenoxy) nicotinamide.

2. The method according to claim 1 in which the weight ratio of (a) to (b) is from 46:1 to 2.3:1 and in which (a) is applied to the locus at a rate of from 570 to 1140 g diclofop-methyl/ha and (b) at a rate of from 25 to 250 g/ha.

3. The method according to claim 1 or 2 in which the application is early post-weed emergence post-crop emergence.

4. A product comprising an effective amount of (a) diclofop-methyl, which is the methyl ester of (R,S)-2-[4-(2,4-dichlorophenoxy) phenoxy]propionic acid, and (b) diflufenican which is N-(2,4-difluorophenyl)-2(3-trifluoromethyl-phenoxy)nicotinamide, as a combined preparation for simultaneous, separate or sequential use in controlling the growth of weeds at a cereal crop locus.

5. A herbicidal composition which comprises an effective amount of (a) diclofop-methyl which is the methyl ester of (R,S)-2-[4-(2,4-dichlorophenoxy)-phenoxy]propionic acid, and (b) diflufenican, in association with a herbicidally acceptable diluent or carrier and/or surface active agent.

6. The herbicidal composition according to claim 5 in which the weight ration of (a) to (b) is from 46:1 to 2.3:1.

7. The herbicidal composition according to claim 5 or 27 which comprises from 0.05 to 90% by weight of diflufenican and diclofop-methyl.

* * * * *